United States Patent
Constancis et al.

(10) Patent No.: US 8,017,156 B2
(45) Date of Patent: Sep. 13, 2011

(54) LONG-ACTING COLLOIDAL INSULIN FORMULATION AND ITS PREPARATION

(75) Inventors: Alain Constancis, Lyons (FR); Florence Nicolas, Saint-Priest (FR); Rémi Meyrueix, Lyons (FR); Olivier Soula, Meyzieu (FR)

(73) Assignee: Flamel Technologies (FR)

( * ) Notice: Subject to any disclaimer, the term of this patent is extended or adjusted under 35 U.S.C. 154(b) by 553 days.

(21) Appl. No.: 11/632,992

(22) PCT Filed: Jun. 9, 2005

(86) PCT No.: PCT/FR2005/050431
§ 371 (c)(1),
(2), (4) Date: Sep. 26, 2008

(87) PCT Pub. No.: WO2006/016078
PCT Pub. Date: Feb. 16, 2006

(65) Prior Publication Data
US 2009/0110742 A1    Apr. 30, 2009

(30) Foreign Application Priority Data
Jul. 19, 2004 (FR) .................................... 04 51578

(51) Int. Cl.
*A61K 9/14* (2006.01)
*A61K 38/28* (2006.01)

(52) U.S. Cl. ...... 424/499; 514/5.9; 514/772.6; 977/773; 977/906

(58) Field of Classification Search .................. None
See application file for complete search history.

(56) References Cited

U.S. PATENT DOCUMENTS

| | | | |
|---|---|---|---|
| 5,656,722 | A | 8/1997 | Dorschug et al. |
| 5,834,422 | A | 11/1998 | Balschmidt et al. |
| 5,904,936 | A | 5/1999 | Huille et al. |
| 6,180,141 | B1 | 1/2001 | Lemercier et al. |
| 7,226,618 | B1 * | 6/2007 | Touraud et al. ............ 424/489 |
| 7,683,024 | B2 | 3/2010 | Chan et al. |
| 2004/0038885 | A1 | 2/2004 | Bryson et al. |

FOREIGN PATENT DOCUMENTS

| | | |
|---|---|---|
| EP | 0 734 720 | 10/1996 |
| FR | 2 801 226 | 5/2001 |
| JP | 2000507934 | 6/2000 |
| JP | 2005531652 | 10/2005 |
| WO | WO-01/37809 | 5/2001 |
| WO | WO 01/37809 | 5/2001 |

OTHER PUBLICATIONS

Constancis et al., *Macromolecular Colloids of Diblock Poly(Amino Acids) that Bind Insulin*, Journal of Colloidal and Interface Science 217(2): 357-368 (1999).
International Search Report for PCT/FR2005/050431, filed Nov. 23, 2005.
Constancis et al., "Macromolecular Colloids of Diblock Poly(Amino Acids) that Bind Insulin", *Journal of Colloid and Interface Science*, (1999), 217(2): 357-368.
Candau, S., Chapter 3: Light Scattering, *Surfactant Solutions*, vol. 22, Ed. R. Zana, M. Dekker, Inc., NY (1987) p. 147-207.
Gatlin et al., "Formulation and Administration Techniques to Minimize Injection Pain and Tissue Damage Associated with Parenteral Products," *Injectable Drug Development, Techniques to Reduce Pain and Irritation*, P.K. Gupta eds., Interpharm Press, Denver, 1999, pp. 401-421.

* cited by examiner

*Primary Examiner* — Jeffrey E Russel
(74) *Attorney, Agent, or Firm* — Patton Boggs LLP

(57) ABSTRACT

The invention relates to injectable long-acting insulin formulations for the treatment of types I and II diabetes in humans and animals.
The essential object of the invention is to provide an injectable long-acting insulin formulation in the form of a colloidal suspension which is stable, which has a good local tolerance and toxicity compatible with the chronic treatment of diabetics, and which maintains a substantial hypoglycemic effect extending over at least 24 hours after a single administration, e.g. by the subcutaneous route.
To achieve this object, the invention relates to a stable aqueous colloidal formulation of insulin-laden nanoparticles of at least one poly(Leu-block-Glu) in which the pH is between 5.8 and 7.0, the osmolarity O (in mOsmol) . . . : $270 \leq O \leq 800$, and the viscosity v (in mPa·s) is low, namely $v \leq 40$. The nanoparticles of poly(Leu-block-Glu) have a mean hydrodynamic diameter Dh such that: $15 \leq Dh \leq 40$.
The invention relates to an antidiabetic drug based on this long-acting insulin formulation and injectable using needles of gauge 29 G, 30 G or 31 G.

12 Claims, No Drawings

LONG-ACTING COLLOIDAL INSULIN FORMULATION AND ITS PREPARATION

CROSS-REFERENCE TO RELATED APPLICATIONS

This application is a national stage application of PCT/FR2005/050431, filed Jun. 9, 2005, which claims priority to FR 04 51578, filed Jul. 19, 2004. The contents of which are incorporated herein in their entirety.

The present invention relates to the field of insulin-based drugs, particularly injectable insulin formulations, for the treatment of types I and II diabetes in humans and animals.

The present invention relates more precisely to injectable insulin formulations formed of colloidal insulin suspensions for daily parenteral administration and capable of maintaining in the diabetic patient or animal, throughout the nyctohemeral period, a serum insulin concentration close to the basal concentration observed in the healthy subject.

The invention further relates to processes for the preparation of said colloidal insulin suspensions.

Diabetics are compelled to undergo a very restricting and imperfect treatment that obliges them to inject themselves with insulin several times a day. Apart from quick-absorbing insulin injections for correcting the rise in glycemia after or during a meal, it is also necessary to maintain the serum insulin at the basal level day and night so as to avoid very harmful side effects. The latter correction is particularly difficult because, at night, patients do not have the opportunity to treat themselves and thus to restore the desirable insulin level.

The injectable insulin formulations have to be stable, i.e. the insulin they contain must not degrade on storage. For example, it must still be fully effective after storage for 2 years at 5° C. The injectable insulin formulations must have a rheology suited to the injection systems commonly used for insulin. There is therefore an acute need for a long-acting insulin formulation that can be injected through very fine needles and is stable. The problem of developing such a formulation has been known for a long time and has formed the subject of numerous studies.

In terms of the present disclosure, "insulin" denotes human insulin, an animal insulin or an insulin analog.

In terms of the present disclosure, a "long-acting insulin formulation" is a formulation that makes it possible on the one hand to avoid any hypoglycemia peak harmful to the patient after administration, and on the other hand to maintain a hypoglycemic action over at least 24 hours.

PRIOR ART

A number of earlier technical proposals for long-acting insulin formulations are referred to below.

Thus, for example, the long-acting human insulin NPH is known. This consists of partially microcrystalline suspensions of human insulin/zinc/protamine complexes (as described e.g. in U.S. Pat. No. 5,834,422), which make it possible to slow down the release of the protein in vivo. In these suspensions the insulin is complexed with protamine and zinc to form a partially crystalline precipitate. After subcutaneous injection the insulin release rate is controlled by the in vivo dissolution kinetics of this precipitate and the insulin decomplexation kinetics. The duration of action of this type of insulin, although longer than that of a rapid insulin, does not exceed 16 hours and does not therefore truly cover the nyctohemeral period. Furthermore, a hypoglycemia peak is observed after administration of this long-acting human insulin NPH, so the latter is not a true long-acting insulin as defined above.

U.S. Pat. No. 5,656,722 has recently described a novel protein structure analogous to insulin; it is called GLARGINE® and is included in a formulation.

A totally different way of obtaining a sustained-release form of protein is disclosed in U.S. Pat. No. B-5,904,936 (EP-B-0 734 720).

The proposed technique consists neither in modifying the insulin chemically, nor in complexing the insulin with protamine and zinc, but rather in adsorbing the human insulin onto biocompatible nanoparticles formed spontaneously by the auto-assembly in water of amphiphilic polyamino acids such as poly(L-leucine-b-sodium glutamate)—hereafter called poly(Leu-block-Glu). This auto-assembly produces a colloidal suspension of nanoparticles. When the human insulin is brought into contact with such a colloidal suspension, it adsorbs spontaneously onto the particles to form a non-covalent insulin/particle complex. After subcutaneous injection the human insulin dissociates gradually from the complex, enabling its plasma concentration to be maintained at a value close to its basal value for a prolonged period of time. The advantage of this approach is that it uses unmodified human insulin and a biocompatible polymer in a non-denaturing process without resorting to potentially denaturing surfactants.

It is stated in Example 14 of U.S. Pat. No. B-5,904,936 that the human insulin associates spontaneously with nanoparticles of poly(Leu-block-Glu) up to a maximum amount of 0.65 mg of human insulin per 10 mg of poly(Leu-block-Glu), i.e. 6.5% by weight. This injectable long-acting insulin formulation according to Example 14 of U.S. Pat. No. B-5,904,936 is capable of improvement in the following respects:

The formulation could benefit from greater injectability, particularly using syringes with 29 G, 30 G or 31 G fine needles. The resulting discomfort for the patient is all the more punishing because of the need for daily injections over several decades.

The formulation could benefit from greater stability to further slow down the degradation of the insulin.

The subcutaneous injection of pigs with this formulation can sometimes lead to the formation of pronounced edema and erythema, indicating that the local tolerance could be improved, so this formulation is poorly compatible with a daily pharmaceutical application over a very long period.

The formulation is difficult to sterilize by filtration.

Example 9 of patent application WO-A-01/37809 describes an injectable long-acting insulin formulation of pH 7.4 which comprises a suspension of nanoparticles of poly(Leu-block-Glu) polymer. This suspension comprises (per ml of preparation): 80 IU of insulin and 56 mg of polymer, i.e. an insulin/poly(Leu-block-Glu) weight ratio of 5%. When administered to beagles at a rate of 2 IU/kg, this suspension affords a sustained release over about 24 hours. However, the stability of this formulation is capable of improvement, as demonstrated in Example 5 of the present patent application, given below.

Supported by this experiment, the Applicant redefined the specifications for an injectable long-acting human insulin formulation:

1. The formulation would benefit from being more easily injectable through a needle of small diameter (e.g. 29 G, 30 G or 31 G) so as to improve the patient's comfort and hence his compliance with the treatment.

2. The insulin formulation is capable of improvement in respect of its stability, especially at 4° C. and room temperature, so that the properties of the formulation are not modified and the human insulin is not degraded.
3. The formulation would be greatly improved if it possessed an excellent local tolerance so as to be compatible with a daily injection over a period of several decades.
4. The bioavailability of the insulin provided by such a formulation would benefit from being as high as possible.
5. The efficacy of the formulation, measured e.g. by its hypoglycemic effect, would benefit from being as high as possible for at least 24 hours after injection.
6. The formulation would benefit from having a rheology that enabled the patient to fill the syringe easily.
7. The ability to be sterilized by filtration would be a decisive asset for the formulation.

Given this state of affairs, one essential object of the present invention is therefore to fully satisfy the specifications described above.

Another essential object of the invention is to provide a long-acting insulin formulation in the form of a colloidal suspension which maintains a substantial hypoglycemic effect extending over at least 24 hours after a single administration, for example by the subcutaneous route.

Another essential object is to provide a long-acting insulin formulation in the form of a colloidal suspension which is stable and which does not modify the structure or bioactivity of the insulin.

Another essential object of the present invention is to provide a long-acting insulin formulation that can easily be injected through a needle of small diameter (for example of gauge 29 G, 30 G or 31 G).

Another essential object of the invention is to provide long-acting insulin formulations in the form of colloidal suspensions that allow a syringe to be filled easily through a needle of small diameter (for example of gauge 29 G, 30 G or 31 G).

Another essential object of the invention is to provide long-acting insulin formulations in the form of injectable colloidal suspensions having a low injection volume and a high concentration of human insulin, typically 100 IU/ml, without detracting from the therapeutic efficacy or, in particular, the duration of the hypoglycemic effect.

Another essential object of the present invention is to provide a long-acting insulin formulation in the form of a colloidal suspension whose good local tolerance and toxicity are compatible with the chronic treatment of diabetics.

Another essential object of the invention is to provide a long-acting insulin formulation in the form of a colloidal suspension in which the insulin is an unmodified human insulin.

Another essential object of the present invention is to provide a long-acting insulin formulation in the form of a colloidal suspension which comprises nanoparticles of poly(Leu-block-Glu) and which can be sterile-filtered on 0.2 µm filters.

Another essential object of the present invention is to provide a long-acting insulin formulation in the form of a colloidal suspension comprising nanoparticles of poly(Leu-block-Glu) onto which the proteins are adsorbed in a reversible, non-covalent manner and without denaturation.

Another essential object of the invention is to provide a colloidal insulin suspension in liquid or dry form which produces a formulation satisfying the specifications referred to above, and which constitutes an appropriate and convenient galenical form for subcutaneous administration.

Another essential object of the invention is to propose a process for the preparation of these long-acting colloidal insulin suspensions, said process being simple to carry out, non-denaturing for the protein and, in addition, always reliably assuring the reproducibility of the characteristics of the formulation.

The above objects, among others, are achieved by the present invention, which relates first and foremost to an injectable long-acting insulin formulation comprising a stable aqueous colloidal suspension of insulin-laden nanoparticles of at least one poly(L-leucine-b-sodium L-glutamate)—hereafter called poly(Leu-block-Glu)—characterized in that:

I—the pH of the formulation is such that:

|  |  |
|---|---|
|  | $5.8 \leq pH \leq 7.0$ |
| preferably | $6.0 \leq pH \leq 7.0$ |

II—the osmolarity O (in mOsmol) of the formulation is such that:

|  |  |
|---|---|
|  | $250 \leq O \leq 800$ |
| preferably | $250 \leq O \leq 600$ |
| and particularly preferably | $270 \leq O \leq 400$ |

III—the viscosity v (in mPa·s) of the formulation, measured by a procedure Mv, is low, namely such that:

|  |  |
|---|---|
|  | $v \leq 40$ |
| preferably | $v \leq 25$ |
| and particularly preferably | $v \leq 20$ |

The inventive basis of this novel colloidal suspension capable of constituting an injectable long-acting galenical insulin formulation lies especially in the combination of parameters I, II & III selected within the following windows:
- a pH window which contributes to the good stability of the suspension forming the injectable long-acting insulin formulation according to the invention,
- an osmolarity window which assures particularly that the formulation has a good local tolerance and a good suitability for sterilizing filtration,
- and a viscosity window which participates in providing the formulation with rheological properties such that a syringe can easily be filled by drawing the formulation through a needle of small diameter (for example of gauge 29 G, 30 G or 31 G).

Another asset of this novel formulation is its reasonable cost.

Finally, and above all, this non-obvious combination of selected parameters I, II & III gives the formulation rheological properties such that it can easily be injected through a needle of small diameter (for example of gauge 29 G, 30 G or 31 G).

Furthermore, the formulation according to the invention preferably possesses at least one (ideally all) of the following characteristics:

a. The osmolarity O of the formulation is adjusted with at least one monovalent or polyvalent (for example divalent or trivalent) salt.
b. The concentration of poly(Leu-block-Glu) is less than 60 mg/ml, preferably between 10 and 55 mg/ml and particularly preferably between 30 and 55 mg/ml.

c. The particles of retained poly(Leu-block-Glu) have a mean hydrodynamic diameter Dh, expressed in nanometers (nm) and measured by a procedure Md, such that:

|  | |
|---|---|
|  | $10 \leq Dh \leq 150$ |
| preferably | $20 \leq Dh \leq 100$ | d. The insulin/poly(Leu-block-Glu) weight ratio, expressed in %, is such that:

|  | |
|---|---|
|  | $3 \leq$ insulin/poly(Leu-block-Glu) |
| preferably | $5 \leq$ insulin/poly(Leu-block-Glu) $\leq 11$ | e. The maximum loading rate of the nanoparticles with insulin, Ta, expressed in % by weight of associated insulin relative to the weight of poly(Leu-block-Glu) and measured by a procedure Ma, is such that:

|  | |
|---|---|
|  | $10 \leq Ta$ |
| preferably | $10 \leq Ta \leq 40$ |
| and particularly preferably | $12 \leq Ta \leq 25$ | f. The insulin is an unmodified human insulin.

Finally, the injectable long-acting insulin formulation according to the invention possesses the following essential properties:
- a good suitability for filling of a syringe by drawing through a needle of small diameter;
- an easy "injectability" through a needle of small diameter, considerably improving the Patient's comfort and hence increasing his compliance with the treatment;
- an excellent stability;
- a good local tolerance;
- a hypoglycemic activity extending over 24 hours after the administration of a standard dose of 0.6 IU/kg to humans;
- a suitability for sterilizing filtration on a 0.2 micron filter by virtue of the small particle size.

This suspension also possesses the property of having:
- a low polymer/insulin weight ratio, limiting the extra cost of polymer;
- a particle size range which assures a good local tolerance and a good suitability for sterilizing filtration;
- a bLE polymer concentration range which enables the hypoglycemic effect to be maintained over at least 24 hours, while at the same time allowing easy injection.

DETAILED DESCRIPTION OF THE INVENTION

The selection of these parameters to give a colloidal insulin suspension that is suitable as an injectable long-acting medicinal insulin formulation is the fruit of substantial and lengthy research involving the measurement and comparison of the pharmacokinetic and pharmacodynamic activities of these insulin formulations on various animal models, and of numerous studies involving the "injectability", stability, tolerance and biocompatibility of this particular suspension, its injectable nature and its ability to be drawn through a needle.

The stable colloidal suspension constituting the formulation contains submicronic structured nanoparticles formed by the auto-assembly of a poly(Leu-block-Glu) copolymer. Said nanoparticles are capable of:

spontaneously associating (adsorbing) the insulin in a non-covalent manner, in colloidal suspension, in the undissolved state and without denaturation, to form a nanoparticle/insulin complex, and releasing the insulin, especially in vivo, in a sustained and/or delayed manner.

Finally, they are stable in the aqueous phase in the absence of surfactant(s).

The colloidal suspension of nanoparticles according to the invention is the result of one particular selection among those described in general terms in WO-A-01/37809. This particular selection was found after numerous tests aimed at optimizing the contradictory requirements of the specifications mentioned above.

It was necessary for the inventors to conduct numerous lengthy tests in order to effect the particular selection of parameters that made it possible to develop a formulation, namely a suspension, that satisfied the specifications mentioned above.

The stability of the suspension is optimized by adjusting the pH of the suspension to between 5.8 and 7.0, preferably to between 6.0 and 7.0 and particularly preferably to less than 7.4. The stability in question is on the one hand a physico-chemical stability of the colloidal suspension of nanoparticles of poly(Leu-block-Glu), and on the other hand a stability of the insulin active principle in terms of therapeutic efficacy (control of glycemia). Advantageously, the formulation remains stable after storage for 2 years at 5° C., for example.

The remarkable ability of the formulation of the invention to be easily injected through a needle of small diameter (for example of gauge 29 G, 30 G & 31 G or diameter 0.15 to 0.4 mm, and of length 8 to 20 mm) is assessed especially by way of the force exerted on the piston of the syringe. For example, it is desirable for this force not to exceed a reasonable value, e.g. in the order of 40 newtons, preferably in the order of 30 newtons, and for the flow rate not to be less than or equal to 1 ml/min. Surprisingly, the viscosity measured at low shear gradient (measured by procedure Mv described below) does not totally control the force needed to inject the colloidal suspension through a needle of small diameter. It is to the Applicant's credit to have shown that the force that has to be applied for injection decreases with the concentration of poly (Leu-block-Glu). Ideally, according to the invention, the concentration of poly(Leu-block-Glu) can be adjusted to optimize the compromise between the duration of action and the injectable nature of the suspension. This optimum is obtained for a polymer concentration of between 10 and 60 mg/ml, preferably of between 20 and 55 mg/ml.

The possibility of easily filling the syringe by drawing the formulation through needles of small diameter (for example of gauge 29 G, 30 G & 31 G or diameter 0.15 to 0.4 mm, and of length 8 to 20 mm) is also an intended feature. Typically, this operation must be carried out e.g. in a time of $\leq 120$ s, preferably of $\leq 60$ s and particularly preferably of $\leq 30$ s for a volume of 500 µl.

It is to the inventors' credit to have established that, in contrast to what was shown regarding the "injectability" of the formulation formed of a colloidal suspension of nanoparticles, the ability of this formulation to allow the rapid filling of a syringe depends substantially on the viscosity (measured by procedure Mv described below) of the suspension. A rapid filling that satisfies the conditions stated above is obtained when the viscosity v (measured by procedure Mv described below) is $\leq 40$ mPa·s, preferably $\leq 25$ mPa·s and particularly preferably $\leq 20$ mPa·s, or in practice $\leq 15$ mPa·s, for example.

Procedure Mv

According to the present invention, the important parameter represented by the viscosity v (in mPa·s at 20° C.) can be determined e.g. at 20° C. using an AR1000 rheometer (TA Instruments) equipped with a cone-and-plate geometry (4 cm, 2°). The viscosity v is measured for a shear gradient of 10 s$^{-1}$.

It is also to be inventors' credit to have found a means of reducing the viscosity by adjusting the osmolarity O (in mOsm) of the suspension to a value of between 270 and 800, preferably of between 270 and 600 and particularly preferably of between 270 and 400.

Preferably, this osmolarity adjustment is effected by adding at least one salt and more especially one or more monovalent and/or polyvalent (e.g. divalent or trivalent) salts, rather than neutral molecules such as glycerol, sucrose or other polyhydroxylated molecules. These salts can be selected e.g. from the following families: sodium chloride, potassium chloride, zinc chloride, sodium or potassium monohydrogenphosphate or dihydrogenphosphate, magnesium or calcium chloride, sodium citrate, sodium sulfate, potassium sulfate or any other salt known to those skilled in the art as being suitable for subcutaneous injection.

According to one noteworthy feature of the invention, polyvalent salts are preferred candidates for the osmolarity adjustment, given that they have a more pronounced fluidizing effect than monovalent salts.

Advantageously, these polyvalent salts are selected e.g. from the group comprising zinc chloride, magnesium chloride, calcium chloride, disodium phosphate, sodium citrate, potassium citrate, sodium sulfate or potassium sulfate, and mixtures thereof.

According to the invention, the nanoparticles are small and, more precisely, have a hydrodynamic diameter Dh (in nm), measured by procedure Md, such that, preferably, in increasing order: 10≦Dh≦150; 10≦Dh≦100; 20≦Dh≦100; 10≦Dh≦50; 15≦Dh≦40.

One of the impacts, among others, of these choices of the size of poly(Leu-block-Glu) particles is that the formulation according to the invention can easily be filtered on a sterilizing filter of 0.2 µm pore size, enabling a sterile injectable formulation to be obtained easily and at lower cost. It is furthermore apparent, surprisingly, that the local tolerance of these particles is better than that of larger particles, as demonstrated in the Examples below.

Procedure Md

The pulverulent powder of poly(Leu-block-Glu) is suspended in water at a concentration of about 50 g/l and the suspension is stirred overnight at 25° C. It is then diluted with 0.15 M aqueous sodium chloride solution to give a final poly(Leu-block-Glu) concentration of between 0.01 and 0.5 g/l and preferably of 0.2 g/l. This suspension is stirred for 1 hour and then introduced into the scattering cell of a Brookhaven light scattering apparatus operating with a vertically polarized laser beam of wavelength 488 nm. The hydrodynamic diameter is calculated from the electric field autocorrelation function by the summation method, as described in the work "Surfactant Science Series" volume 22, Surfactant Solutions, Ed. R. Zana, chap. 3, M. Dekker, 1984.

According to another preferred feature, the poly(Leu-block-Glu) polymers selected according to the invention have the following characteristic:
the maximum loading rate of the nanoparticles with insulin, Ta, expressed in % by weight of associated insulin relative to the weight of poly(Leu-block-Glu) and measured by a procedure Ma, is such that:

|  | 10 ≦ Ta |
|---|---|
| preferably | 10 ≦ Ta ≦ 40 |
| and particularly preferably | 12 ≦ Ta ≦ 25 |

Procedure Ma (a) Preparation of aqueous solutions of insulin: Lyophilized recombinant human insulin is poured into a volume V of 0.01 N hydrochloric acid solution over at most 15 min. This solution is then poured into the same volume V of 0.01 N NaOH solution. The pH is adjusted to between 7.2 and 7.4 with 1 N sodium hydroxide solution. The solution is stirred gently for 30 min. The weight of insulin and the volume V are calculated as a function of the desired volume V' of final solution to give insulin concentrations of 100 IU/ml, 120 IU/ml and 140 IU/ml.

(b) Preparation of the insulin formulation: Lyophilized poly(Leu-block-Glu) is added to the insulin solutions at a rate of 11 mg/ml. These mixtures are degassed, then placed in a tilting stirrer at 25° C. for 2 hours, and then degassed again. The pH is adjusted to between 7.2 and 7.4 with 1 N HCl solution and the mixtures are stirred (tilting stirrer) overnight at room temperature.

(c) Assay of the free insulin: The formulations are injected onto a size exclusion liquid chromatography column under non-dissociating conditions and the free insulin is assayed by fluorimetry.

In one advantageous variant, the insulin associated with the nanoparticles in the suspension constituting the formulation of the invention is an unmodified insulin.

In terms of the invention, an unmodified insulin is a recombinant or non-recombinant insulin which has not undergone any transformation of its primary structure or any modification of the side groups of the amino acids.

Advantageously, the suspension constituting the formulation of the invention comprises at least one preservative preferably selected from the group comprising phenols, cresols (e.g. metacresol), methyl, propyl or butyl parahydroxybenzoate or any other preservative known to those skilled in the art (reference may be made e.g. to the article by L. A. Gatlin et al. in *Injectable Drug Development*, P. K. Gupta, Interpharm Press, Denver, Colo., 1999) and mixtures thereof.

The process for the synthesis of poly(Leu-block-Glu) and the process for the preparation of the nanoparticles of poly(Leu-block-Glu) in aqueous suspension are preferably carried out according to the modalities and recommendations described in WO-A-01/37809.

Instead of being in stable suspension in an aqueous liquid medium, the insulin-laden nanoparticles of poly(Leu-block-Glu) could also exist in a stable solid state, preferably in pulverulent form. Thus the present invention further relates to a solid, preferably a pulverulent solid, characterized in that it comprises insulin-laden nanoparticles of poly(Leu-block-Glu) and in that it is obtained from the above-defined liquid suspension constituting the formulation of the invention. This is done by any known and appropriate means such as lyophilization, atomization or drying.

The process for the preparation of the injectable long-acting liquid insulin formulation involves poly(Leu-block-Glu) that is not laden with insulin, and consists essentially in suspending at least one poly(Leu-block-Glu) and insulin in an aqueous liquid medium, preferably with stirring, optionally adding excipients, adjusting the pH to a value of between 5.8 and 7.0 if necessary, and optionally filtering the resulting suspension on a filter of pore size 0.2 µm.

Association of the insulin with the nanoparticles can be effected by several methods, non-limiting Examples of which are given below.

In a first method, the insulin is associated with the particles by bringing an aqueous phase containing insulin into contact with the colloidal suspension of nanoparticles of poly(Leu-block-Glu). More precisely, an isotonic suspension of nanoparticles of neutral pH is reconstituted to a concentration of 60 mg/ml or more (according to the desired concentration of the final suspension). A concentrated insulin solution (typically of between 500 and 600 IU/ml—pH between 7 and 8—isotonic) is then prepared from insulin powder (dissolution in an acid medium, followed by neutralization) for immediate use. The two solutions are mixed by stirring for a few minutes and this phase is optionally followed by a "maturation" phase of a few hours. The pH is then adjusted to a value of between 5.8 and 7.0.

A second method consists essentially in bringing the poly (Leu-block-Glu) in the pulverulent state into contact (by mixing) with an aqueous phase containing insulin at a concentration e.g. of between 100 and 200 IU/ml.

It is important to pay attention to one of the essential features of the invention, namely establishing a pH of between 5.8 and 7.0, preferably of between 6.0 and 7.0. This factor plays an important part in the stability and local tolerance of the suspension of nanoparticles of poly(Leu-block-Glu). The pH can be adjusted by any known and appropriate means, namely especially by acidification, for example in the following manner:
- -1- addition of 0.1 N hydrochloric acid to the insulin-laden suspension (an intermediate precipitate is then produced which disappears after stirring for about one hour);
- -2- addition of 0.1 N acetic acid to the insulin-laden suspension (no intermediate precipitate).

The addition of acetic acid (-2-) is preferred.

When the formulation according to the invention is prepared, it is optionally possible to add excipients, to readjust the pH to a value of between 5.8 and 7.0 if necessary, and optionally to sterilize the resulting suspension by filtration on 0.2 micron pores.

These other excipients can be especially at least one preservative preferably selected from the group comprising phenols, cresols (e.g. metacresol), methyl, propyl or butyl parahydroxybenzoate or any other preservative known to those skilled in the art (reference may be made e.g. to the article by L. A. Gatlin et al. in *Injectable Drug Development*, P. K. Gupta, Interpharm Press, Denver, Colo., 1999) and mixtures thereof.

The mixing conditions, both for the regulation of pH and for the addition of excipients, are conventional and within the competence of those skilled in the art, especially in terms of temperature, pressure and stirring.

Finally, the liquid suspension can be converted to a pulverulent solid by any conventional method known to those skilled in the art, such as lyophilization, atomization or drying.

According to another of its features, the invention relates to the pharmaceutical and veterinary applications of the poly (Leu-block-Glu)/insulin suspension. The essential application is the treatment of diabetes and, more precisely, types I and II diabetes.

Thus the invention further relates to a drug, characterized in that it comprises a formulation containing a colloidal poly (Leu-block-Glu)/insulin suspension, this formulation being as defined above, and/or a formulation obtained by the process also described above, and/or a pulverulent solid as defined above.

The drug is preferably one that is intended for the treatment of diabetes and, more precisely, types I and II diabetes.

According to one advantageous provision of the invention, the drug to which it relates is comparable to an injectable long-acting liquid human insulin formulation that is capable of providing the diabetic patient, after a subcutaneous injection, with a basal insulin concentration for at least 24 hours in a regime of repeat injections.

In the present disclosure, the basal insulin concentration shall be understood as a typical blood concentration observed in the healthy individual, i.e. 30 picomol/l.

The invention further relates to a method of treating diabetes, particularly types I and II diabetes, characterized in that it consists essentially in administering to the patient the above-mentioned drug based on a formulation containing a stable aqueous colloidal suspension of nanoparticles of poly (Leu-block-Glu) laden with insulin, preferably unmodified insulin.

The method preferably involves a daily administration by injection, preferably subcutaneous injection.

The drug according to the invention can also take the form of a pulverulent solid described above and optionally an aqueous liquid for preparing the suspension.

Consequently, the invention also covers a galenical presentation comprising on the one hand a pulverulent solid as defined above, and on the other hand, separately, an aqueous liquid with which the suspension constituting the formulation according to the invention is reconstituted before administration.

The Examples which follow will provide a better understanding of the invention in its different product/process/application features. These Examples illustrate the preparation of the formulation according to the invention based on a suspension of insulin-laden nanoparticles of poly(Leu-block-Glu); they also present the structural characteristics and the properties of this formulation by comparing it with poly(Leu-block-Glu)/insulin formulations according to the prior art.

EXAMPLES

Example 1

Synthesis of a 25/35 Diblock poly(Leu-block-Glu)

38.9 g of NCA-GluOMe (0.208 mol) and 156 g of N-methylpyrrolidin-2-one (NMP) are introduced, with stirring, into a 0.5 liter reactor thermostatted at 30° C. After dissolution, 5.78 g of a 0.452 M solution of ammonia in methanol (1.25 mol %/NCA) are added. Polymerization is monitored by measurement of the carbon dioxide released in a gas bell jar, and verified by disappearance of the vibrational bands characteristic of NCAs at 1860 and 1790 $cm^{-1}$. After 30 min, a solution of 23.3 g of NCA-leucine (0.149 mol) in 5219 g of NMP is introduced. After a reaction time of 10 min, the temperature is raised to 60° C. Polymerization is monitored as above. It is complete after 1-2 hours. The temperature of the reaction mixture obtained above is raised to 80° C. 42.0 g of aqueous hydrochloric acid (35% by weight) are added to the reaction medium over 30 min, with mechanical stirring. The reactor is then placed under reduced pressure, set at 600 mbar, for 6 hours. A mixture of 42.0 g of 35% hydrochloric acid and 167.9 g of water is then added over 60 min, this being followed by a second vacuum phase at 250 mbar for 18 hours. The reaction mixture is subsequently cooled to 50° C. and then neutralized with aqueous sodium hydroxide solution (35% by weight). The NMP and the sodium chloride formed in the neutralization are removed by diafiltration against 20 volumes of Milli Q water on a 1000 dalton MWCO membrane (Pellicon II system, Millipore). This gives a stable aqueous colloidal suspension of carrier nanoparticles. The suspension of nanoparticles is finally lyophilized.

The contents of leucine units are determined by proton nuclear magnetic resonance (signals at 2.10, 2.22 and 2.58 ppm for 4 H of the Glu and at 0.85 ppm for 6 H of the Leu).

Example 2

Synthesis of a 25/70 Diblock poly(Leu-block-Glu)

146.4 g of NCA-GluOMe are dissolved in 586 g of NMP, to which 18.43 g of a 0.48 M solution of ammonia in methanol are added. When the polymerization of the NCA-GluOMe is complete, a solution of 43.9 g of NCA-Leu in 708 g of NMP is introduced and polymerization of the NCA-Leu is monitored until the monomers have disappeared. The medium is then heated to 80° C. and 129.4 g of 35% HCl are added dropwise over 30 min to 1 hour. A vacuum of 600 mbar is applied for 6 hours, after which a further 129.4 g of 35% HCl, mixed with 517.5 g of water, are added. A vacuum of 250 mbar is then applied for 18 hours. After this step the temperature is lowered to 50° C. and 1 liter of water is introduced, followed by 280 ml of 35% NaOH to bring the pH to 7.4. The solution is then filtered (5 μm), dialyzed in water (cut-off threshold 1000 Da) to remove the solvent and the salts, and finally filtered (0.22 μm). This suspension can be used direct or be subjected to further treatments such as distillation of the water or lyophilization.

Example 3

Preparation of a Long-Acting Insulin Suspension According to the Invention 3.1—Preparation of an Intermediate Colloidal Suspension of Nanoparticles of poly(L-leucine-block-sodium L-glutamate) (P) Having a Concentration of 60 mg/g:

The suspension is prepared under a laminar flow hood or in a sterile room.

50 g of poly(Leu-block-Glu) polymer according to Example 2 in lyophilized form (containing about 1% of water) and 757 g of water for injection are introduced successively into a 3 l glass flask. The suspension is stirred vigorously with a magnetic stirrer bar for at least 12 hours. A limited vacuum (50-100 mbar) is created in the flask. 10.6 g of 30% NaCl and 6.7 g of 1 N NaOH are added to the solution in order to adjust the pH to 7.2, the osmolarity to 300 mOsm and the polymer concentration to 60 mg/ml.

3.2—Preparation of an Intermediate Insulin Solution Having a Concentration of 590 IU/ml:

4.5 g of recombinant human insulin (powder) with an activity of 28.4 IU/g and a moisture content of 7.7% are introduced into a glass flask, 181 g of water are added and the insulin is dispersed, with slow magnetic stirring. 4.0 g of 1 N HCl are added to give a clear acidic insulin solution. 5.6 g of 1 N sodium hydroxide solution are then added to give a final solution with a pH of between 7 and 8. 6.1 g of 30% NaCl are added to adjust the osmolarity.

The solution is filtered on a 0.2 μm polyethersulfone membrane before being mixed with the suspension of NPs.

3.3—Preparation of an Excipient Solution (140 mM phenol, 140 mM m-cresol, 0.1 N Acetic Acid):

The following are introduced successively into a 1 l flask:
13.2 g of phenol (M=94 g/mol)
100 g of water
15.1 g of m-cresol (M=108 g/mol)
100 g of 1 N acetic acid
771.7 g of water The solution is stirred for at least half an hour to give a clear solution, and is then filtered on a 0.2 μm PVDF or PTFE membrane.

3.4—Preparation of a Long-Acting Colloidal Insulin Suspension A:

(Osmolarity O=300 mOsm; pH=6.5; concentration of poly(Leu-block-Glu) Cpol=42 mg/ml; concentration of insulin Cinsulin=3.5 mg/ml)

800 g of suspension P are introduced into a 1 liter flask.
196 g of insulin solution having a concentration of 590 IU/ml are added, with slow magnetic stirring. Stirring is maintained for ¼ hour and the mixture is then left to stand at 25° C. overnight. 171 g of excipient solution are then added to the mixture and the solution is stirred for 4 hours. The resulting formulation is filtered on a 0.2 μm polyethersulfone membrane.

Example 4

Viscosity and Hydrodynamic Diameter of the Long-Acting Insulin Suspension A According to the Invention The viscosity measurements are made at 20° C. on an AR1000 rheometer (TA Instruments) equipped with a cone-and-plate geometry (4 cm, 2°). The viscosity is measured for a shear gradient of 10 s$^{-1}$.

A viscosity of 25 mPa·s is found.

The hydrodynamic diameter of the particles of the suspensions H, M and L, measured by procedure Md, is 35 nm.

Example 5

Comparative Stabilities of the Long-Acting Insulin Suspensions at Different pH Values A first pharmaceutical insulin suspension M containing:
100 IU/ml of recombinant human insulin
42 mg/ml of the poly(Leu-block-Glu) polymer according to Example 1
21 mM phenol and metacresol is prepared according to Example 3 above. Its pH is adjusted to 6.5±0.1 and its osmolarity is 300±20 mOsmol.

A second comparative long-acting pharmaceutical insulin suspension, Comp1, identical to the composition M, is prepared in the same manner except that, in contrast to the suspension according to the invention, its pH is adjusted to 7.2±0.1. The osmolarity O is again 300±20 mOsmol.

The pharmaceutical suspensions M and Comp1 are subjected to accelerated stability testing at 37° C. The stability is monitored by measuring the pH, the osmolarity, the hydrodynamic diameter of the insulin-laden nanoparticles and the amount of non-denatured insulin in each of the preparations A and B as a function of time.

To assay the insulin in the preparations M and Comp1, 0.1 ml of preparation is dissolved in 2 ml of trifluoroacetic acid (TFA). The solution is then injected into a Biobasic® C8 column for HPLC analysis of the protein. This affords an assay of the non-denatured insulin in the preparation. The time limit of the preparation is reached when the proportion of non-denatured insulin drops below 95%.

The pH, the osmolarity and the diameter of the nanoparticles are stable for the two preparations M and Comp1, as shown in the Table below.

Table 1 below shows the change in pH, osmolarity and hydrodynamic diameter of the particles and in the % of non-denatured human insulin for the formulations M (pH 6.5) and Comp1 (pH 7.4).

TABLE 1

| Time (days) | 0 | 7 | 21 |
|---|---|---|---|
| pH | | | |
| M | 6.5 | 6.3 | 6.5 |
| Comp1 | 7.2 | 7.3 | 7.2 |
| Osmolarity O (mOsmol) | | | |
| M | 303 | 301 | 305 |
| Comp1 | 297 | 302 | 301 |
| Hydrodynamic diameter (nm) | | | |
| M | 36 | 34 | 35 |
| Comp1 | 35 | 35 | 34 |
| % non-denatured insulin | | | |
| M | 100 | 98 | 96 |
| Comp1 | 100 | 95 | 86 |

It is seen that the suspension M according to the invention, maintained at pH 6.5, has an excellent stability under these accelerated test conditions, since 95% of the insulin is still non-denatured after 21 days. On the other hand, for the formulation Comp1 at pH 7.2, the amount of non-denatured insulin drops below 95% as from t=7 days. Thus, surprisingly, the stability of the insulin in the long-acting insulin preparations according to the present invention is remarkably good at slightly acidic pH.

Example 6

Comparison of the Local Tolerance of a Long-Acting Insulin Suspension According to the Invention and a Long-Acting Insulin Suspension Based on a poly(Leu-block-Glu) According to WO-A-01/37809 and Not Belonging to the Selection According to the Invention A study was carried out to compare the local tolerance of the suspension H according to the invention, corresponding to Example 3 above, and a formulation of a poly(Leu-block-Glu) of neutral pH that does not belong to the selection according to the invention.

The suspension M according to the invention comprises:
100 IU/ml of recombinant human insulin
42 mg/ml of the poly(Leu-block-Glu) polymer according to Example 3
21 mM phenol and metacresol
and is prepared according to Example 3 above. Its pH is adjusted to 6.5±0.1.

A comparative suspension Comp2, not belonging to the invention, is prepared from a poly(Leu-block-Glu) copolyamino acid according to WO-A-01/37809. It comprises:
100 IU/ml of recombinant human insulin
100 mg/ml of a poly(L-leucine-block-sodium L-glutamate) formed of 40 units of leucine and 60 units of sodium glutamate, the hydrodynamic diameter of the particles being 80 nm
This formulation Comp2 is prepared by the procedure described in Example 3 above. Its pH is adjusted to 7.4±0.1.

The suspensions M and Comp2 above and 0.9% NaCl solution (negative reference) were injected subcutaneously, in a volume of 0.50 ml, into the abdomen of 9 domestic pigs.

The clinical signs—erythema and edema—were evaluated for three days following the injection.

The negative reference (NaCl) caused no clinical reaction.

The preparation Comp2 caused a local reaction which increased up to 24 hours. At this stage it is characterized by erythema and edema graded as moderate to pronounced. The reaction disappears in about 3 days.

The preparation M induced a very slight and transitory local reaction. A few animals exhibit very slight erythema after 12 and 24 hours and very slight edema is generally observed up to 24 hours.

Thus the local tolerance of the suspension M according to the invention is notably better than that of the suspension Comp2.

In contrast to Comp2, the suspension M according to the invention therefore allows daily administration of the drug.

Example 7

Filling Time for a Formulation A According to the Invention

The filling time of a syringe through a needle of gauge 29 and length 8 mm is measured for increasing osmolarity values.

The suspension according to the invention is prepared according to Example 3. It has a pH of 6.5 and a concentration of 43 mg/ml.

The filling volume is 0.5 ml.

The osmolarity O of the suspension is adjusted by adding metered amounts of NaCl.

The results obtained are shown in Table 2 below:

TABLE 2

| Osmolarity O (mOsmol) | Filling time (s) |
|---|---|
| 120 | filling impossible |
| 200 | 180 |
| 300 | 90 |
| 600 | 50 |

Adjusting the osmolarity O according to the invention thus makes it possible to shorten the filling time of a syringe sufficiently to easily allow a daily usage by patients.

The invention claimed is:

1. Injectable long-acting insulin formulation comprising a stable aqueous colloidal suspension of insulin-laden nanoparticles of at least one poly(L-leucine-b-sodium L-glutamate)—hereafter called poly(Leu-block-Glu)—characterized in that:
   I—the pH of the formulation is: $5.8 \leq pH \leq 7.0$
   II—the osmolarity O (in mOsmol) of the formulation is: $270 \leq O \leq 800$
   III—the viscosity v (in mPa·s) of the formulation, measured by a procedure Mv, is: $v \leq 40$.

2. The formulation according to claim 1, comprising at least one monovalent or polyvalent salt.

3. The formulation according to claim 1, wherein the concentration of poly(Leu-block-Glu) is less than 60 mg/ml.

4. The formulation according to claim 1, wherein the insulin/poly(Leu-block-Glu) weight ratio, expressed in %, is such that: $3 \leq insulin/poly(Leu\text{-}block\text{-}Glu)$.

5. The formulation according to claim 1, wherein the maximum loading rate of the nanoparticles with insulin, Ta, expressed in % by weight of associated insulin relative to the weight of poly(Leu-block-Glu) and measured by a procedure Ma, is such that: $10 \leq Ta$.

6. The formulation according to claim 1, wherein the insulin is an unmodified human insulin.

7. The formulation according to claim 1, wherein said formulation further comprises at least one preservative selected from the group consisting of phenols, cresols, methyl parahydroxybenzoate, propyl parahydroxybenzoate, butyl parahydroxybenzoate and mixtures thereof.

8. A method for the preparation of the formulation of claim 1 said method comprising
mixing at least one poly(Leu-block-Glu) and insulin in an aqueous liquid medium,
stirring,
adjusting the pH to a value of between 5.8 and 7.0, and
filtering the resulting suspension.

9. A method for the preparation of the formulation of claim 1 said method comprising
mixing the poly(Leu-block-Glu) in a pulverulent state with an aqueous phase containing insulin.

10. A drug that comprises an injectable long-acting insulin formulation according to claim 1.

11. Drug according to claim 10, characterized in that it is intended for the treatment of diabetes.

12. Drug according to claim 10 wherein said drug is capable of providing a diabetic patient with a basal insulin level for at least 24 hours after a subcutaneous injection.

* * * * *